United States Patent [19]

Hickerson

[11] Plant 4,417

[45] May 15, 1979

[54] APHELANDRA PLANT

[76] Inventor: Norman E. Hickerson, Box 1148, Apopka, Fla. 32703

[21] Appl. No.: 905,580

[22] Filed: May 15, 1978

[51] Int. Cl.[2] ..... A01H 5/00

[52] U.S. Cl. ..... Plt./88

[58] Field of Search ..... Plt./88

*Primary Examiner*—Robert E. Bagwill

*Attorney, Agent, or Firm*—Duckworth, Hobby, Allen & Pettis

[57] ABSTRACT

A sport of an *Aphelandra squarrosa* plant characterized by distinctive and attractive leaf color, which leaves exhibit a purplish red coloration in their midrib, petiole and abaxial surface of the blade.

1 Drawing Figure

BACKGROUND

The invention described herein is a new and distinct variety of Aphelandra plant discovered by me in the greenhouses of Hickerson Flowers, Inc. at Altamonte Springs, Fla. The new variety was obtained as a sport from *Aphelandra squarrosa* "Apollo"(U.S. Plant Pat. No. 3,507, dated Mar. 5, 1974). The new variety was selected by me as a single variant plant from a crop of the parent variety being grown under my direction and control.

The sport was noted and selected due to its unique foliar pigmentation. The sport is distinct from the parent variety "Apollo" and from all other Aphelandra varieties of which I am aware in having a red pigment providing the principal color to the leaf midrib, petiole, and lower leaf blade surface. The presence of red pigmentation results in a desirably striking and commercially valuable contrast between darkly pigmented and white to lightly pigmented areas of the variegated foliage.

Asexual reproduction of my new Aphelandra variety was performed by me by cuttings at Altamonte Springs, Fla., with its distinct and characteristic traits stable and perpetuated through successive propagations.

DRAWINGS

The accompanying photographs show typical specimen plants of my new variety in color as nearly true as it is reasonably possible to make the same in a color photograph of this character.

DETAILED DESCRIPTION OF THE PLANT

The following is a detailed description of my new Aphelandra variety as based on observation of specimen plants grown in Altamonte Springs, Fla. Color terminology is in accordance with the Universal Color Language and the ISCC-NBS Color-Name Charts with Centroid Colors distributed by the U.S. National Bureau of Standards.

Parentage: Sport of Acanthaceae: *Aphelandra squarrosa* "Apollo".

Propagation: Holds its distinguishing leaf color characteristics through successive propagations by cuttings.

PLANT

Habit: Herbaceous perrenial.

Growth: The full height attainable has not been determined because of the plants being used for cuttings, but is expected to range in height from 18 inches to 24 inches with a spread of approximately 14 inches on mature plants; upright and branched.

STEM

Terete with a diameter from ¼ to ⅝ inch in diameter. Nodes not noticeably swollen but having a line encircling the same. Stem color is 257 very deep purplish red.

LEAVES

Placement: Opposite.

Shape: Blade simple, ovate to ovate-elliptic, tips accuminate, margin entire or wavy, petiole generally terete with adaxial surface flattened.

Size: Blade commonly up to 8 inches or more in length and 4 inches or more in width, petiole ¼ inch to ½ inch in length.

Texture: Waxy.

Color of adaxial surface of blade: Variegated with lightly and darkly pigmented areas. Lightly pigmented areas covering 70% or more of the upper leaf surface and color is 263 white to 104 pale greenish yellow over lateral veins blending gradually into interveinal areas to 121 pale yellow green. Colors of upper surface of midrib at basal end of blade is 257 very deep purplish red which fades gradually moving toward the leaf tip to 252 pale purplish pink near the tip. Irregular patches of darkly pigmented tissue occur in interveinal areas of the leaf blade and are 147 very dark green.

Color of abaxial surface of blade: Variegated with lightly and darkly pigmented areas. Lightly pigmented areas have green as the predominant hue and cover 40% or less of the blade areas. Lightly pigmented areas occur as interveinal tissue near the midrib and adjacent to the lateral veins and are 263 white to 148 very pale green. Tissues covering the abaxial surface of the midrib are variegated being 257 very deep purplish red at the base of the blade and becoming gradually replaced by patches of 135 light yellowish green tissue toward the leaf tip. Darkly pigmented tissues occur interveinally occupying 60% or more of the interveinal leaf area with red as the predominant hue and color of 262 grayish purplish red to 259 dark purplish red.

Color of petiole: 257 very deep purplish red.

FLOWERS

No flowers have been observed on the new sport. Like its parent, the new sport is expected to flower rarely under the growing conditions used to date.

I claim:

1. A new and distinct variety of Aphelandra plant substantially as herein described, characterized particularly as to novelty by a distinctive and attractive leaf-color having a purplish red pigment in sub-epidermal tissues of the leaves and being particularly evident in both adaxial and abaxial surfaces of the leaf midrib and in coloration of the abaxial surfaces of the leaf blade.

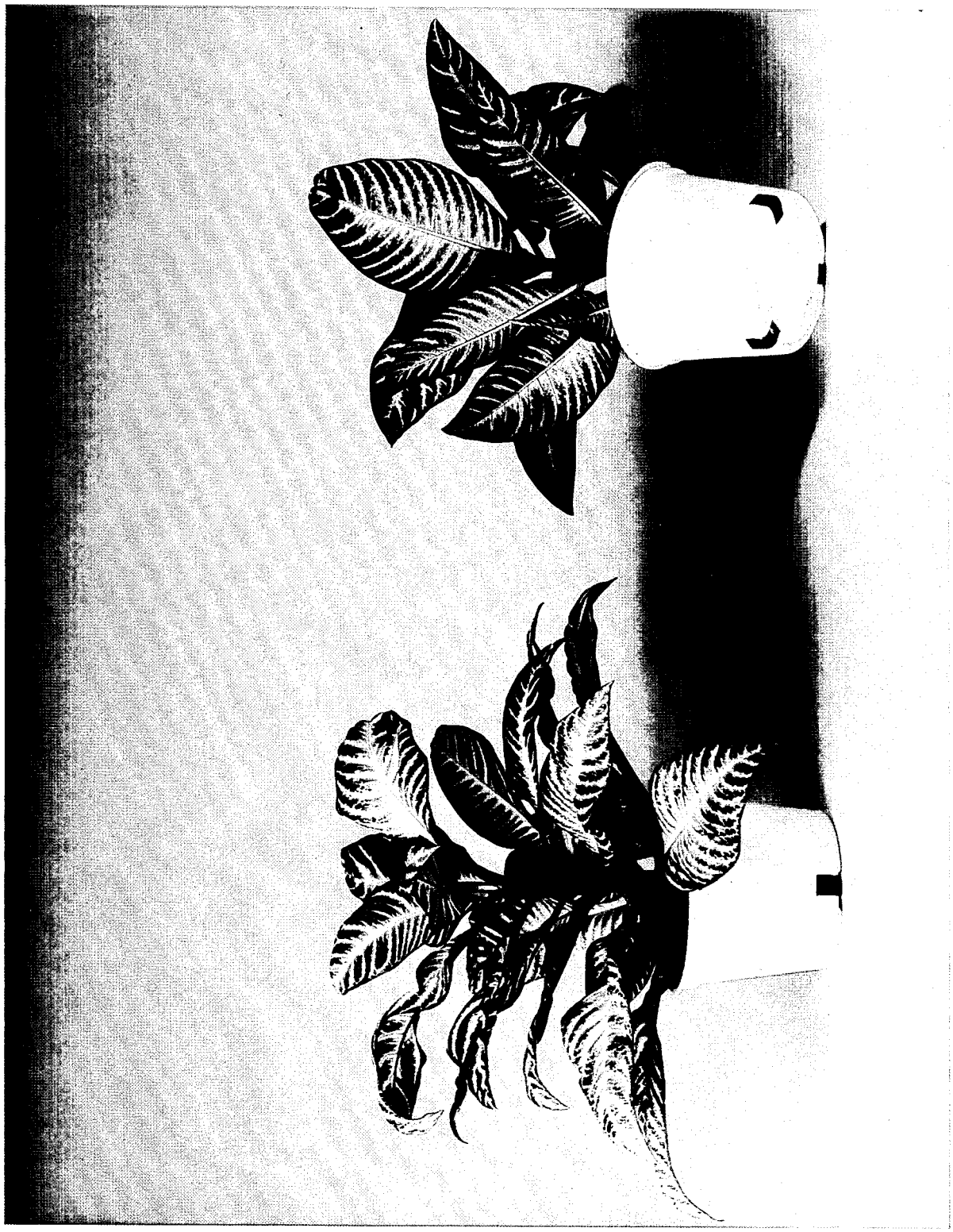

* * * * *